(12) United States Patent
Niemann et al.

(10) Patent No.: US 9,709,493 B2
(45) Date of Patent: Jul. 18, 2017

(54) SENSOR DEVICE FOR DETECTING MOISTURE ON A PANE

(71) Applicant: Hella KGaA Hueck & Co., Lippstadt (DE)

(72) Inventors: Thomas Niemann, Delmenhorst (DE); Torsten Eggers, Bremen (DE)

(73) Assignee: HELLA KGAA HUECK & CO., Lipstadt (DE)

( * ) Notice: Subject to any disclaimer, the term of this patent is extended or adjusted under 35 U.S.C. 154(b) by 396 days.

(21) Appl. No.: 14/157,128

(22) Filed: Jan. 16, 2014

(65) Prior Publication Data

US 2014/0196525 A1   Jul. 17, 2014

(30) Foreign Application Priority Data

Jan. 17, 2013   (DE) ........................ 10 2013 000 751

(51) Int. Cl.
| | | |
|---|---|---|
| *G01N 21/55* | (2014.01) | |
| *B60S 1/08* | (2006.01) | |
| *G01N 21/552* | (2014.01) | |

(52) U.S. Cl.
CPC ............ *G01N 21/55* (2013.01); *B60S 1/0833* (2013.01); *G01N 21/552* (2013.01); *B60S 1/0837* (2013.01)

(58) Field of Classification Search
CPC .............................. G01N 21/55; B60S 1/0833
USPC ........................................................... 73/73
See application file for complete search history.

(56) References Cited

U.S. PATENT DOCUMENTS

| | | | | |
|---|---|---|---|---|
| 6,052,196 | A * | 4/2000 | Pientka | B60S 1/0822 250/227.25 |
| 6,634,225 | B1 * | 10/2003 | Reime | B60S 1/0837 340/602 |
| 7,847,255 | B2 * | 12/2010 | Teder | B60S 1/0822 250/341.8 |
| 9,335,264 | B2 * | 5/2016 | Kroekel | B60S 1/0844 |
| 2011/0128543 | A1 * | 6/2011 | Choi | B60S 1/0833 356/342 |
| 2011/0204206 | A1 * | 8/2011 | Taoka | B60S 1/0844 250/208.1 |
| 2015/0070499 | A1 * | 3/2015 | Roelke | G03B 15/00 348/148 |

FOREIGN PATENT DOCUMENTS

| | | | |
|---|---|---|---|
| DE | 42 09 680 A1 | 9/1993 | |
| DE | EP 0562275 A1 * | 9/1993 | ............ B60S 1/0822 |
| DE | 197 46 351 A1 | 10/1998 | |
| DE | 19746351 A1 * | 10/1998 | ............ B60S 1/0822 |
| DE | 19815748 A1 * | 10/1999 | ............ B60S 1/0822 |
| DE | 198 15 748 C2 | 3/2000 | |
| DE | 103 47 977 A1 | 5/2005 | |
| DE | 103 55 205 A1 | 7/2005 | |

(Continued)

*Primary Examiner* — Lisa Caputo
*Assistant Examiner* — Jamel Williams
(74) *Attorney, Agent, or Firm* — Muncy, Geissler, Olds & Lowe, P.C.

(57) ABSTRACT

In a sensor device for detecting moisture on a pane comprising at least one transmitter which emits light which is reflected at the pane and received by at least one receiver, an optical system is provided between the transmitter and the receiver, which brings about a multiple reflection between the pane and the optical system. A particularly good measurement is thereby made possible.

11 Claims, 3 Drawing Sheets

(56) References Cited

FOREIGN PATENT DOCUMENTS

| | | |
|---|---|---|
| DE | 10 2004 015 040 A1 | 10/2005 |
| DE | WO 2006040241 A1 * | 4/2006 ............ B60S 1/0822 |
| DE | 10 2008 044 003 A1 | 5/2010 |
| EP | 0 444 520 A2 | 9/1991 |
| FR | EP 2367052 A1 * | 9/2011 ........... G02B 13/001 |

* cited by examiner

SENSOR DEVICE FOR DETECTING MOISTURE ON A PANE

The invention relates to a sensor arrangement for detecting moisture on a pane, comprising a transmitter which emits light which is reflected at the pane and received by a receiver, wherein an optical system is provided between the transmitter and the receiver, which brings about a multiple reflection between the pane and the optical system.

A sensor device, which is also designated as rain sensor or rain-light sensor is described, for example, in EP 1 339 565 B1. Provided there in combination with a support plate for a camera is a rain sensor in which in three different optical guide elements each having a transmitter, measuring radiation is emitted into the pane, this is reflected at the outer side of the pane and received by the receiver. The light is reflected on the outer side of the pane. If the pane outer side is wet, the reflection behaviour changes and a larger proportion of the light is coupled out and not reflected. The presence of moisture on the pane surface and therefore rain can then be concluded from the signal thus varied.

Similar rain-light sensors in combination with camera modules are described in DE 10 2008 044 003 A1 and DE 103 55 205 A1. Further sensor devices are described in DE 198 15 748 C2, DE 42 09 680 A1, DE 103 47 977 A1, DE 197 46 351 A1, DE 10 2004 015 040 A1, U.S. Pat. No. 7,847,255 B2 and EP 0 444 520 A2.

It is the object of the invention to provide a sensor device of the type mentioned initially with which a particularly good measurement is possible.

In a sensor device for detecting moisture on a pane comprising a transmitter which emits light which is reflected on the pane and received by a receiver, where an optical system is provided between the transmitter and the receiver, which brings about a multiple reflection between the pane and the optical system, it is provided as essential to the invention that the sensor device has a frame which can be fastened to the pane, that the optical system extends in an annular shape around the entire frame and that the frame of the sensor device serves to hold further components, in particular a camera. The frame is provided and designed for further components. As a result, a particularly good measurement can be achieved in a comparatively small installation space. The accuracy of the measurement is significantly increased by the multiple reflection.

To this end the sensor device preferably has a mirror which is disposed parallel to the pane. The light beam is reflected multiply to and fro between this mirror and the pane. If the pane is wet, a portion of the light, beam is not reflected at the pane but coupled out so that the reflected portion is reduced. The light used here can be in the visible range, in the infrared range or in the ultraviolet range. Transmitters and receivers are preferably configured as corresponding diodes. Transmitters and receivers are spaced apart from one another at the ends of the optical system, in particular disposed at the ends of the mirror.

In a preferred embodiment of the invention the sensor device has a frame. The frame can preferably be fastened to the pane. The frame can be circular, oval or angular, preferably square. Preferably the frame has an opening in the inner region through which it is possible for further sensors or other components to have access to the pane. The frame of the sensor device is preferably also used as a holder for further components, in particular for a camera. The camera in this case then has a field of view through the opening of the frame. The frame is preferably square and particularly preferably trapezoidal. The sensor device can therefore preferably serve two purposes with the frame, namely firstly the provision of a rain-light sensor and on the other hand, accommodating a camera or a camera module or another sensor element. As a result, an integration of installation space and a particularly space-saving arrangement of two elements are accomplished.

In a preferred embodiment of the invention, the optical system of the sensor device is disposed on the inner side of the frame. The optical system including the appurtenant electronics can then be disposed as an independent assembly inside the frame. The fixing of the optical system on the frame can be accomplished, for example, by means of a spring element. Fundamentally it is also feasible to dispose the optical system on the outer side of the frame or in a recess of the frame extending in the longitudinal direction. The optical system extends at least over a subregion of the frame. Preferably however the optical system is disposed along at least one side of the frame and preferably on at least two sides of the frame. In a particularly preferred embodiment the optical system extends in an annular shape over the entire frame. As a result a maximum utilisation of the possible detectable area and therefore a particularly accurate measurement is achieved. The optical system is preferably designed so that the incident light is reflected at an angle between 40° and 60° between the optical system, in particular the mirror of the optical system and the windscreen.

In a preferred embodiment of the invention the optical system comprises special optical correcting elements which are disposed on the optical system, i.e. opposite the windscreen, and serve to collimate the incident light beams and to focus the outgoing light beams. In this way a multiple reflection is made possible between the optical system and the windscreen at high intensity. Preferably the optical system is designed so that the reflection angle at the optical system is greater than the reflection angle at the pane. Preferably the reflection at the optical system is accomplished at less than 46° and that at the pane at less than 44° C.

The sensor device is preferably provided for a motor vehicle and for attachment to the windscreen. The camera used then serves as a front camera for monitoring the road in front of the motor vehicle.

A further aspect of the invention relates to the provision of a motor vehicle with a windscreen and a sensor device of the type described above disposed on the windscreen.

The invention is explained in further detail hereinafter with reference to a preferred exemplary embodiment shown in the drawing. In detail in schematic view.

Figure 1:
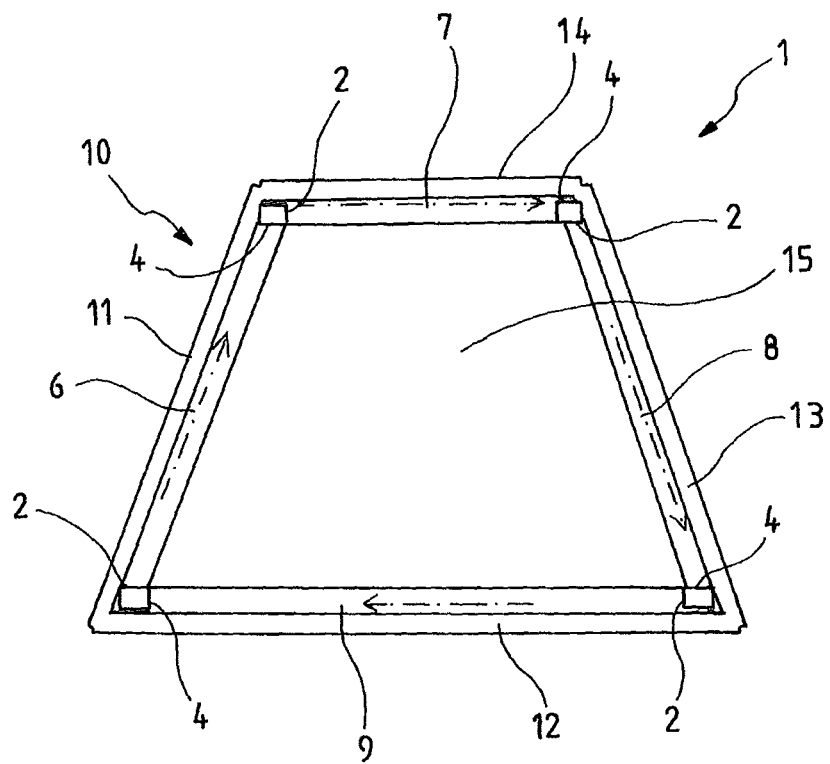
FIG. 1 shows a plan view of a first embodiment of the sensor device according to the invention.

FIG. 1 shows a sensor device 1 with a frame 10. The frame is here configured to be trapezoidal. The four sides of the frame are characterised by 11, 12, 13 and 14. On the inner side of the frame an optical system is provided which is here divided into four subsections which are assigned to the individual frame elements. The individual optical systems are characterized by 6, 7, 8 and 9. In the four corner regions of the frame transmitting diodes 2 and receiving diodes 4 are provided. These can be configured as separate diodes or also as a single diode, which performs both functions. In the embodiment shown in FIG. 1 four measurement sections are formed along the individual straight sections. The transmitting diode 2 emits a light beam. This can be either in the visible range, in the infrared range or in the ultraviolet range. This is guided by a suitable optical system at an angle of about 45° towards the pane, at which it is reflected and returned to the optical system of the corresponding section 6, 7, 8, 9 and from this is again reflected at an angle of about 45°. A multiple reflection of the light beam therefore takes place along the sections 6, 7, 8, 9 until this is again received by the receiver 4 which is formed by a diode. From the decrease in the intensity of the light beam it can be determined what fraction of the light has been coupled out. This fraction of the light is dependent on the degree of wetting of the pane. The frame 10 is provided and equipped with its four frame sides 11, 12, 13, 14 for attachment to the pane, in particular the windscreen of a motor vehicle. The frame has a through opening 15 in the central region. Through this the field of view through the pane is opened for other components, in particular for a camera or a camera module which is fastened or will be fastened on the frame 10.

Figure 2:
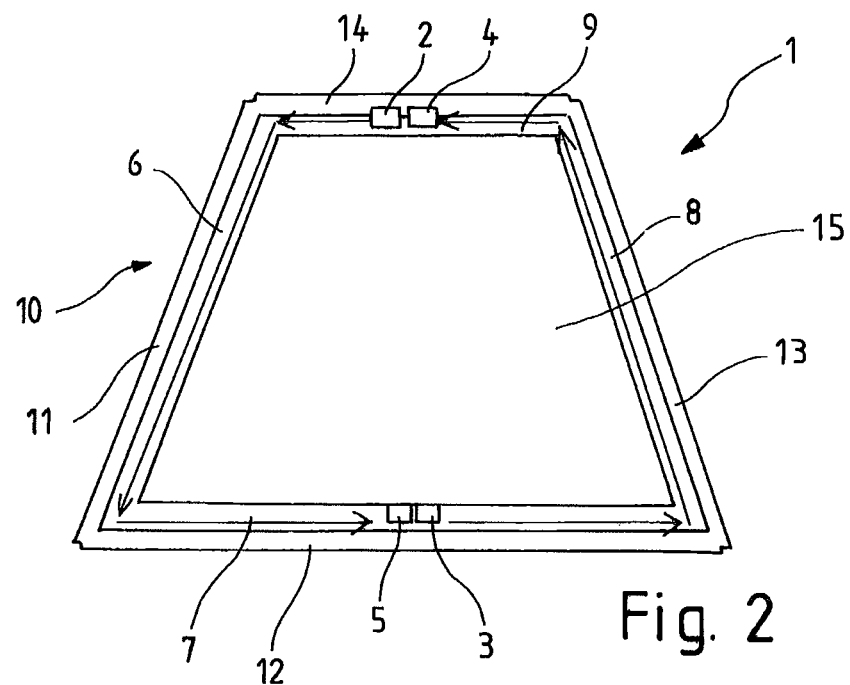
FIG. 2 shows a plan view of a second embodiment of the sensor device according to the invention.

FIG. 2 shows a second embodiment of the invention. The same parts are characterised by the same reference numbers. Here the transmitting diodes 2 and 3 and the receiving diodes 4 and 5 of the individual optics 6, 7, 8, 9 are not disposed in the corners but on two opposite sides. Corresponding reflecting deflecting optical systems are provided in the corners so that the light beam emitted by the transmitters 2 and 3 runs as far as the corresponding receivers 4 and 5.

Figure 3:
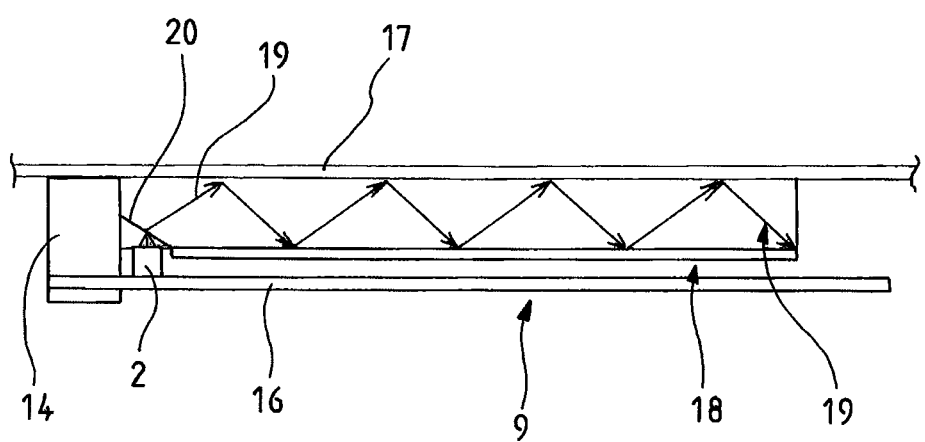
FIG. 3 shows a cutaway sectional view of the sensor device according to the invention.

FIG. 3 shows a cross-sectional view through the optical system 9. On the outside left a frame component 14 can be seen, adjacent to which a transmitter 2 is disposed. The transmitter 2 is configured as a diode which emits a light beam 19 upwards. This is refracted by an optical element 20 and thereby emitted at an angle of about 45°, preferably less than 44° onto the pane 17, which is preferably a windscreen of a motor vehicle and is then reflected at this angle at the pane 17. The reflected light beam 19 is then reflected at a mirror 18 of the optical system 9 and reflected back to the pane at an angle of about 45°, preferably at an angle of 46°. The mirror 18 is preferably configured as a mirror layer which is disposed parallel to the pane 17. The beam 19 is in this way reflected multiply to and fro between the mirror 18 and the pane 17. As a result of the multiple reflection, the sensitive surface is enlarged many times. If a droplet impinges upon this surface of the pane 17, the reflection beam is thus reduced.

Figure 4:
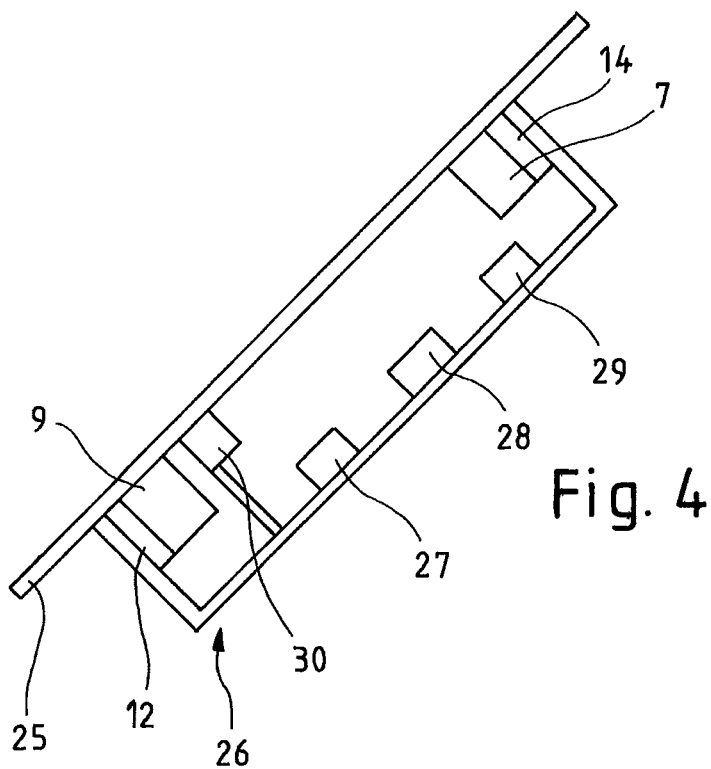
FIG. 4 shows a cutaway side view of a first application of the invention.

FIG. 4 shows in a cutaway side view a pane 25 which in FIG. 4 runs from bottom left to top right. The previously described sensor device 1 is fastened to this pane. In the cutaway sectional view, in particular the lower frame side 12 and the upper frame side 14 of the frame can be seen in section. On the frame 10 the measuring sections 9 and 7 of the optical system are disposed on the inner sides thereof, by which means the degree of wetting of the pane is determined. The optical system can thus also be designated as rain optics. Here a sensor module 26 is attached to the frame, in particular plugged on or clipped one. The sensor module 26 is configured as a cover or in the manner of a cover and various sensors are disposed in the interior of the sensor module 26, which are positioned in such a manner that the sensor field is directed onto or through the pane 25 through the through opening 15 of the frame 10 (compare FIGS. 1 and 2). In particular, a light sensor 27, a solar sensor 28 and an HUD (head-up display) sensor 29 are disposed here. Furthermore, the sensor module 26 here favourable also has a moisture sensor 30 which detects the moisture of the inner side of the pane and is connected to the sensor module 26 at least for data evaluation. The moisture sensor 30 can be fastened to the housing of the sensor module 26 by means of a web and then come in touching contact with the pane 25 during assembly.

Figure 5:
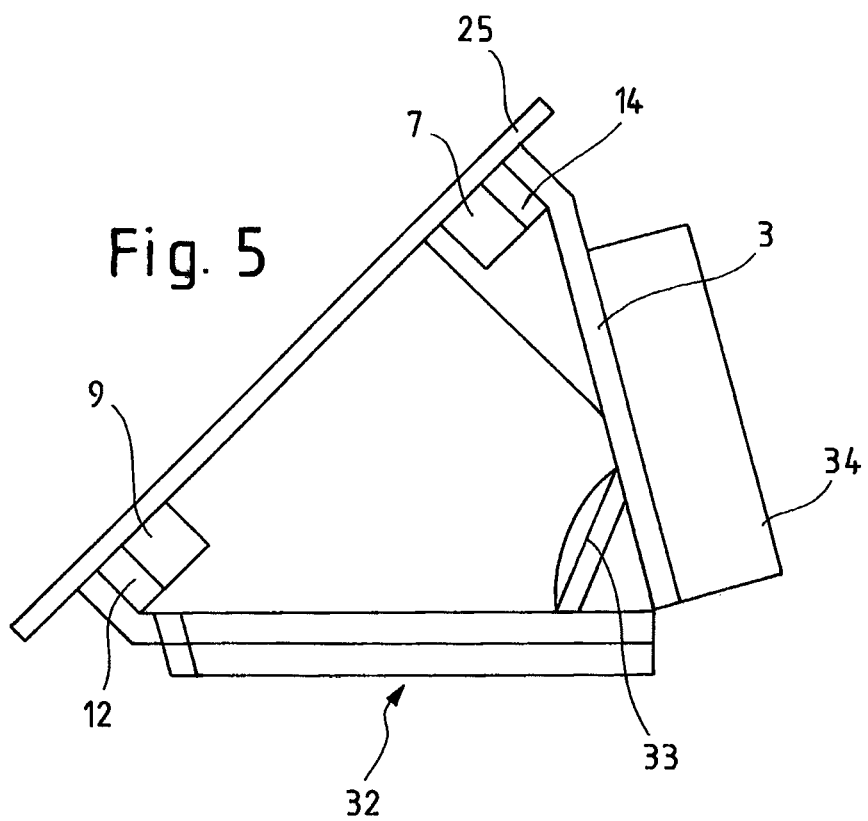
FIG. 5 shows a cutaway side view of a second application of the invention.

In another embodiment of the invention in FIG. 5 the pane 25 is again shown with a sensor device according to the invention disposed thereon. Here also in the cutaway side view, of the frame 10, the frame sides 12 and 14 and the rain optics disposed on the it side thereof with the measuring sections 9 and 7 can be identified. Instead of the sensor module 26 as in FIG. 4, here a camera module 32 is now fastened to the frame. This camera module 32 in particular comprises a camera 33 with corresponding optics and appurtenant electronics 34. The camera replaces the individual sensors. Only the rain optics cannot be simulated by the camera. In this respect in the embodiment according to FIG. 5, there is an appropriate combination of the rain optics with the camera.

The invention claimed is:

1. A sensor device for detecting moisture on a pane comprising at least one transmitter which emits light which is reflected at the pane and received by at least one receiver,
   wherein an annular optical system is provided between the only one transmitter and the only one receiver, which brings about a multiple reflection between the pane and the optical system,
   wherein the sensor device has a frame which can be fastened to the pane,
   wherein the frame has an annular shape,
   wherein each side of the annular optical system is parallel with a corresponding side of the annular frame, and
   wherein the annular optical system is disposed on the inner periphery side of the annular frame, facing a center of the annular frame.

2. The sensor device according to claim 1, wherein the optical system has a mirror which is disposed parallel to the pane.

3. The sensor device according to claim 1, wherein the one transmitter and the one receiver are configured as diodes.

4. The sensor device according to claim 1, wherein the optical system is designed such that the multiple reflection takes place at angles between 40° and 50°.

5. The sensor device according to claim 1, wherein the optical system is configured in such a manner that the angle of reflection at the pane is smaller than the angle of reflection in the optical system.

6. A motor vehicle having a windscreen and the sensor device according to claim 1 disposed on the windscreen.

7. The sensor device according to claim 1, wherein the frame of the sensor device is used for holding a component.

8. The sensor device according to claim 7, wherein the component is a camera.

9. The sensor device according to claim 5, wherein
   the optical system has a mirror which is disposed parallel to the pane, and
   the angle of reflection at the pane is smaller than the angle of reflection at the mirror.

10. The sensor device according to claim 1, wherein the entire frame is annularly disposed on a surface of the pane.

11. The sensor device according to claim 1, wherein the optical system extends in parallel with the entire frame.

* * * * *